US008852269B2

(12) United States Patent
Yu et al.

(10) Patent No.: US 8,852,269 B2
(45) Date of Patent: Oct. 7, 2014

(54) CLOSED LOOP FILAMENT STENT

(75) Inventors: Woong-Ryeol Yu, Seoul (KR); Ju-Hyun Kim, Seoul (KR); Suk-Jin Hong, Incheon (KR); Joon-Seok Lee, Gyeongsan-si (KR); Jae-Heung Yoo, Gunpo-si (KR)

(73) Assignee: Seoul National University Industry Foundation, Seoul (KR)

( * ) Notice: Subject to any disclaimer, the term of this patent is extended or adjusted under 35 U.S.C. 154(b) by 1263 days.

(21) Appl. No.: 11/788,928

(22) Filed: Apr. 23, 2007

(65) Prior Publication Data

US 2007/0265696 A1 Nov. 15, 2007

(30) Foreign Application Priority Data

May 11, 2006 (KR) .................. 10-2006-0042627

(51) Int. Cl.
*A61F 2/06* (2013.01)
(52) U.S. Cl.
USPC .................. 623/1.51; 623/1.15; 623/1.53
(58) Field of Classification Search
USPC ................... 623/1.5, 1.51, 1.52, 1.53
See application file for complete search history.

(56) References Cited

U.S. PATENT DOCUMENTS

| 4,655,771 | A | | 4/1987 | Wallsten | |
|---|---|---|---|---|---|
| 5,061,275 | A | | 10/1991 | Wallsten et al. | |
| 5,630,840 | A | | 5/1997 | Mayer | |
| 5,645,559 | A | | 7/1997 | Hachtman et al. | |
| 6,083,257 | A | * | 7/2000 | Taylor et al. | 623/1.46 |
| 6,146,417 | A | * | 11/2000 | Ischinger | 623/1.15 |
| 6,792,979 | B2 | * | 9/2004 | Konya et al. | 140/92.1 |
| 6,942,690 | B1 | * | 9/2005 | Pollock et al. | 623/1.15 |
| 7,462,192 | B2 | * | 12/2008 | Norton et al. | 623/1.53 |
| 2004/0098099 | A1 | * | 5/2004 | McCullagh et al. | 623/1.15 |

FOREIGN PATENT DOCUMENTS

| EP | 1287790 | 8/2003 |
|---|---|---|
| KR | 10-1999-0045770 | 6/1999 |
| WO | WO 0105331 A1 * | 1/2001 |

* cited by examiner

*Primary Examiner* — Thomas J Sweet
*Assistant Examiner* — Matthew Schall
(74) *Attorney, Agent, or Firm* — Edwards Wildman Palmer LLP; Kongsik Kim

(57) ABSTRACT

Disclosed is a stent having a hollow tubular structure with open ends which tubular structure is formed by a plurality of filaments woven alternately, wherein each of the filaments has at least one elongated closed-loop wire and both ends of each of the filaments are positioned at the open ends, and a method for fabricating the stent.

8 Claims, 5 Drawing Sheets

CLOSED LOOP FILAMENT STENT

CROSS-REFERENCE TO RELATED APPLICATION

The present application claims, under 35 U.S.C. §119, the benefit of Korean Patent Application No. 10-2006-0042627, filed May 11, 2006, the entire contents of which are hereby incorporated by reference.

BACKGROUND OF THE INVENTION

1. Technical Field

The present invention relates to a stent for use in implantation in a patient and a fabrication method thereof, and more particularly to a stent which is self-expandable and can deliver drugs tropically, and a fabrication method thereof.

2. Background Art

Expandable medical prostheses, so-called stents, are known and commercially available. They are disclosed generally in U.S. Pat. No. 4,655,771 (Wallsten), U.S. Pat. No. 5,061,275 (Wallsten et al.) and U.S. Pat. No. 5,645,559 (Hachtmann et al.), for example. Stents are used within blood vessels for various medical applications. For example, there are intravascular stents for treating stenoses, and stents for maintaining openings in urinary, biliary, tracheobronchial, oesophageal and renal tracts and inferior vena cava.

Commonly used materials for known stent filaments are Elgiloy™ and Phynox™ metal spring alloys. Other metallic materials that can be used for expandable stent filaments include 316 stainless steel, MP35N alloy and superelastic Nitinol nickel-titanium. Another expandable stent disclosed in, for example, U.S. Pat. No. 5,630,840 to Mayer has a radiopaque clad composite structure. Expandable stents may be made of a titanium alloy.

For example, EP 1287790 (Schmitt & Lentz) discloses an axially flexible braided stent that is self-expandable due to the elastic memory of the braided polymer fibers. The braided fibers are shaped into a tube at or slightly below the melting temperature of the polymer, and then longitudinally stretched upon cooling.

To date, stents have been mainly hand-made and the productivity is significantly low. Also, such prior art stents are difficult to have uniform characteristics (elasticity and/or self-expandability) over their entire length. For example, prior art stents have irregular distances between metallic wires defined therein.

Alternatively, a braiding apparatus has been used to produce stents. Thus-produced stents, however, have a problem. That is, since the stents have at their end portions metal filaments the end portions of which are exposed, additional process is required to weld the exposed end portions of the metal filaments to each other. This problem is aggravated when a stent is composed of fine filaments having a relatively small diameter; from the practical point of view, it is almost impossible to weld the end portions of such a stent.

Korean Patent Application Publication No. 1999-45770, for example, suggests a technique for the purpose of solving the above-described problems, which discloses a stent in which beads are welded at the ends of filaments constituting a stent body. However, this technique still has problems. First, it is not easy to weld fine particles of beads to ends of the filaments having a fine diameter. Further, when welding of the beads is not perfectly performed, there can be undesirable exposure of a sharp tip portion of stents, which may damage blood vessels of a patient.

SUMMARY OF THE INVENTION

The present invention has been made to provide a stent and a method for fabricating the stent which solve the above-described problems of the prior art. It is an object of the present invention to provide a stent which is formed of a plurality of filaments having a closed-loop shape to ensure uniformity of a stent and safety in its use. It is another object of the present invention to provide a method for fabricating the stent, which can easily manufacture the stent by a so-called pre-welding technique that braids a plurality of assembly lines in which the both ends of a guide line are connected to one closed-loop filament, respectively.

In one aspect, the present invention provides a stent having a hollow tubular structure formed by a plurality of filaments woven alternately. Each of the filaments has at least one elongated closed-loop wire and both ends of each of the filaments are positioned at open ends of the tubular structure.

Preferably, the plurality of filaments comprise two groups of closed loops which are arranged spirally in a longitudinal direction of the tubular structure and alternate with each other in opposite directions. Also preferably, each of the filaments is made of a biocompatible metal or an alloy thereof. In addition, the filament can also preferably be made of a polymeric material. The polymeric material may include polyester, polypropylene, polyethylene, polyurethane, polynaphthalene, polytetrafluoroethylene, expanded polytetrafluoroethylene, silicone, and combinations thereof.

Suitably, the elongated closed-loop filament has a pair of parallel parts which are substantially in contact with each other. Also suitably, the filament has a pair of parallel parts which are spaced from each other at predetermined distances.

The tubular structure can be formed by, preferably, braiding and/or winding the plurality of closed-loop filaments.

In another aspect, the present invention provides a method for fabricating a stent, comprising the steps of: (a) preparing a plurality of filaments having at least one elongated closed-loop wire; (b) forming a plurality of assembly lines, in each of which at least one closed-loop filament is connected with at least two guide lines in an alternating fashion; (c) braiding the assembly lines into a tubular structure by providing the plurality of the assembly lines to a braiding device; and (d) removing the braided guide lines from both ends of the tubular structure composed of the filaments.

Preferably, the method may further comprise the step of subjecting the filaments to a first heat treatment to fix a shape of the closed-loop filaments prior to the step (b).

Also preferably, the method may further comprise the step of subjecting the stent to a second heat treatment to memorize a shape of the stent next to the step (d).

Suitably, in the method, each of the assembly lines has at least two closed-loop wire filaments connected with a guide line so that the at least two closed-loop filaments are positioned alternately with the guide lines.

In an embodiment, the step (a) may further comprises the step of bending both ends of each of the closed-loop wire filaments in advance so as to fix a shape of each of the closed-loop wire filaments.

BRIEF DESCRIPTION OF THE DRAWINGS

The accompanying drawings illustrate preferred embodiments of the present invention, and technical spirit of the present invention will be more fully described in combination with the following detailed description, so it should be understood that the scope of the present invention is not limited to the accompanying drawings.

DESCRIPTION OF THE PREFERRED EMBODIMENTS

Figure 1:
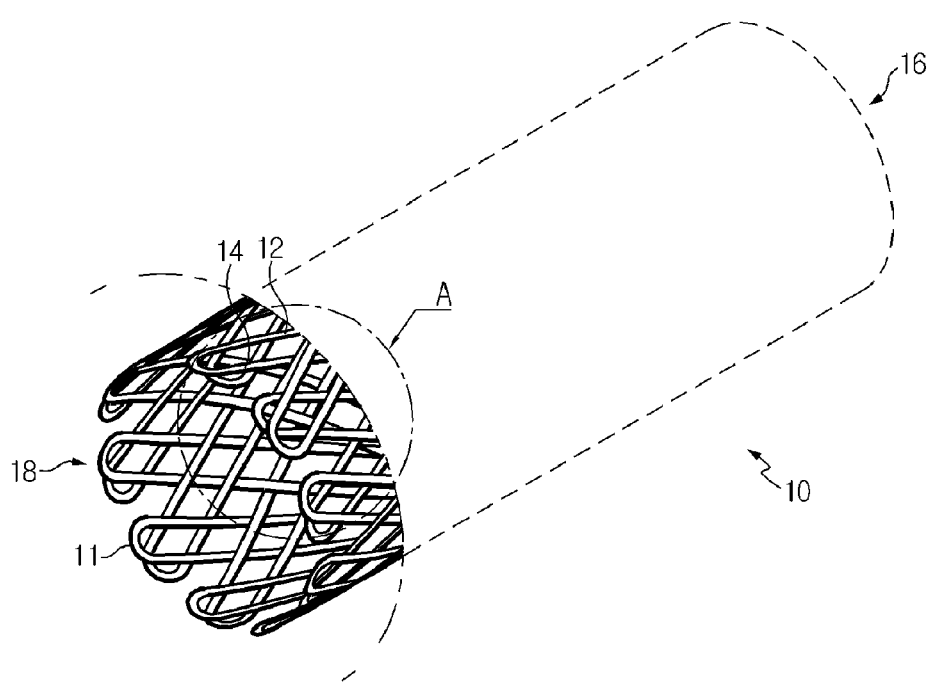
FIG. 1 is a perspective view schematically showing a stent according to a preferred embodiment of the present invention.

According to a preferred embodiment of the present invention, the closed-loop wire filament may be produced using various processes in addition to the above-described welding process. For example, closed-loop wire filaments may be produced by heating and melting a metal such as surgical steel and, particularly, a polymeric material over the melting temperature and pouring them into a molding cast that has the same shape as a closed-loop wire filament to be produced, or by sliding a cylindrical tube, which is made of metals, polymeric materials, etc., into filaments having a fine diameter. In the processes, the polymeric material may be selected from the group consisting of polyester, polypropylene, polyethylene, polyurethane, polynaphthalene, polytetrafluoroethylene, expanded polytetrafluoroethylene, silicone, and combinations thereof.

The stent according to a preferred embodiment is formed of right-handed filaments having a closed-loop wire and left-handed filaments having a closed-loop wire, wherein the right-handed filaments are composed of a plurality of elongated wires arranged in right handed helices in their longitudinal direction, and the left-handed filaments are composed of elongated wires arranged in left handed helices in their longitudinal direction and have the same number as that of the right-handed filaments. The left/right-handed filaments are woven to each other in one-over/one-under pattern to form a tubular structure having both open ends. Accordingly, in the hollow tubular structure with both open ends of the stent, both open ends of each of the closed-loop wire filaments start from one open end of a stent and are helically woven to reach the other end of the stent.

In order to ensure structural stability of a stent, each of the closed-loop wire filaments is formed in at least one helical turn. The number of helical turns of the closed-loop wire filaments in the stent is preferably determined by desired uses and specifications of the stent. Also, the number of the closed-loop wire filaments may be differently determined by both desired sizes and diameters of the open ends of the stent when the closed-loop wire filaments are expanded and contracted in a radial direction of the stent, and diameters of the wires used for each of the filaments. Accordingly, both the diameters of the wires and the number of the closed-loop wire filaments have an effect on the flexibility of the stent whose filaments are contracted in a radial direction during the expansion of the stent.

Also, the closed-loop filament is preferably made from wires having a round section. Alternatively, the closed-loop filament may be made from wires having a rectangular section, depending on specific applications and uses of the stent.

One way to alternately form closed-loop wire filaments is generally preformed by alternately weaving two groups of closed-loop wire filaments in opposite directions in a one-over/one-under pattern, but the present invention is not limited thereto. It goes without saying that other patterns of forming for the stent, such as one-over/two-under pattern, two-over/two-under pattern, etc., may be used herein.

According to still another preferred embodiment of the present invention, the elongated closed-loop filament preferably has a pair of parallel parts which are substantially in contact with each other. In the stent configured as in the above, each of the closed-loop filaments has two wires overlapped with each other, but end portions of each of the closed-loop filaments form a round loop in the open ends of the stent. Therefore, it is possible to prevent damage on human blood vessels and the like by means of the open ends of the stent which are composed of the round portion of the filaments of the stent.

As a substitute, in the stent according to the preferred embodiment of the present invention, the elongated closed-loop filament preferably has a pair of parallel parts which may be arranged apart from each other at predetermined distances.

According to a preferred embodiment of the present invention, the closed-loop wire filaments are made of, for example, metals such as surgical steel, etc., and have good elasticity which is, for example, similar to alloys such as high cobalt stainless steel, Elgiloy alloys, etc. These materials enable the stent to show good self-expandability.

According to another preferred embodiment of the present invention, some or all of the filaments are preferably made from shape memory alloys such as Nitinol since, in addition to the self-expandability, mechanical characteristics of the stent should be changed according to temperature.

According to still another preferred embodiment of the present invention, in order to minimize an adverse and undesirable interaction with walls of blood vessels and/or blood flowing through the blood vessels, the closed-loop wire filament preferably has a biocompatible coating composed mainly of polymer materials. Such a coating enables the stent to deliver drug agents.

According to yet another preferred embodiment of the present invention, the stent is preferably manufactured by braiding a plurality of closed-loop wire filaments using a known braiding machine, and the stent may also be hand-made alone or made in combination of the hand-made process and a braiding process.

Hereinafter, preferred embodiments of the present invention will be described in detail referring to the accompanying drawings. Prior to the description, it should be understood that the terms used in the specification and appended claims should not be construed as limited to general and dictionary meanings, but interpreted based on the meanings and concepts corresponding to technical aspects of the present invention on the basis of the principle that the inventor is allowed to define terms appropriately for the best explanation. Therefore, the description proposed herein is just a preferable example for the purpose of illustrations only, not intended to limit the scope of the invention, so it should be understood that other equivalents and modifications could be made thereto without departing from the spirit and scope of the invention.

Figure 2:
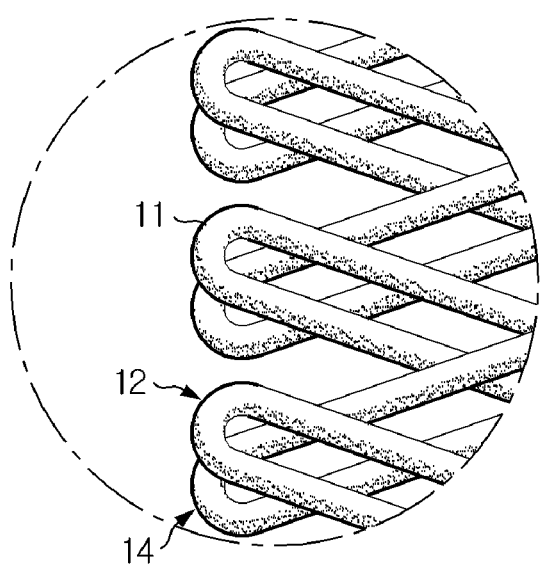
FIG. 2 is a partial exploded view taken from a section "A" of FIG. 1.

FIG. 1 is a diagram showing a stent according to a preferred embodiment of the present invention, and FIG. 2 is a perspective view taken from a section "A" of FIG. 1.

Referring to FIGS. 1 and 2, a stent 10 according to a preferred embodiment of the present invention comprises a plurality of right-handed closed-loop filaments 12 and a plurality of left-handed closed-loop filaments 14. The right-handed closed-loop filaments 12 include a plurality of elongated wires spirally arranged in right handed helices in their longitudinal direction. Similarly, the left-handed closed-loop filaments 14 include a plurality of elongated wires spirally arranged in left handed helices in their longitudinal direction. The number of elongated wires of the right-handed closed-loop filaments 12 is the same as that of the left-handed closed-loop filaments 14. The left/right-handed filaments 12, 14 are woven to each other in the one-over/one-under pattern to form a tubular structure having both open ends 16, 18. The open ends 16, 18 of each of the closed-loop wire filaments 12, 14 start from one open end of the stent 10 and are helically woven to reach the other end of the stent 10.

Preferably, the closed-loop filaments 12, 14 used in this embodiment can be made of Nitinol wires whose sections are round in shape. A contact point 3 (see FIG. 5) of the closed-loop filaments 12, 14 is preferably positioned in a substantially central region in a longitudinal direction of the stent 10.

In the stent 10, each of the closed-loop filaments 12, 14 has a pair of wires arranged in parallel with each other, and the parallel wires are substantially spaced apart from each other. Also, end portions 11 of each of the closed-loop filaments in the open ends 16, 18 of the stent 10 are formed in a ring shape.

Figure 3:
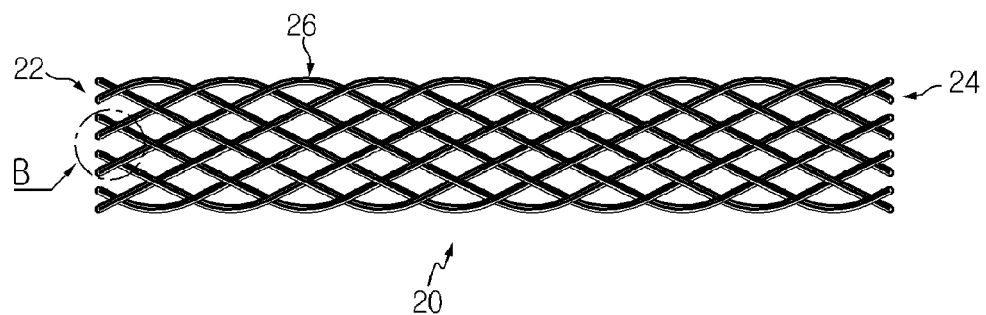
FIG. 3 is a perspective view schematically showing a stent according to another preferred embodiment of the present invention.
Figure 4:
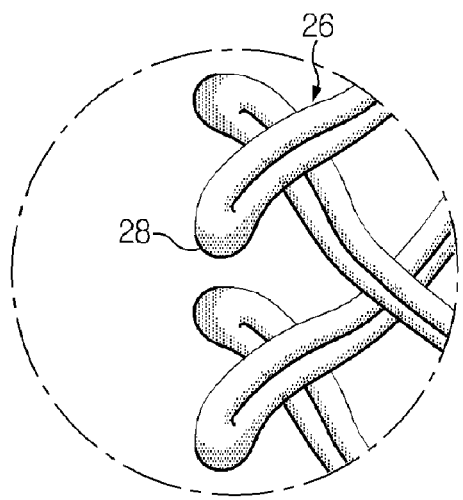
FIG. 4 is a partial exploded view taken from a section "B" of FIG. 3.

FIG. 3 is a diagram showing a stent according to another preferred embodiment of the present invention, and FIG. 4 is an exploded perspective view taken from a section "B" of FIG. 3.

Referring to FIGS. 3 and 4, the stent according to this embodiment includes both open ends 22, 24 and therefore each of the closed-loop filaments 26 has a pair of wires arranged in parallel with each other, and the parallel wires are in contact with each other in a longitudinal direction. That is to say, ends of each of the filaments 26 in the open ends 22, 24 of the stent 20 do not have a sharp portion but a round portion 28 where the wires are bended.

Figure 5:
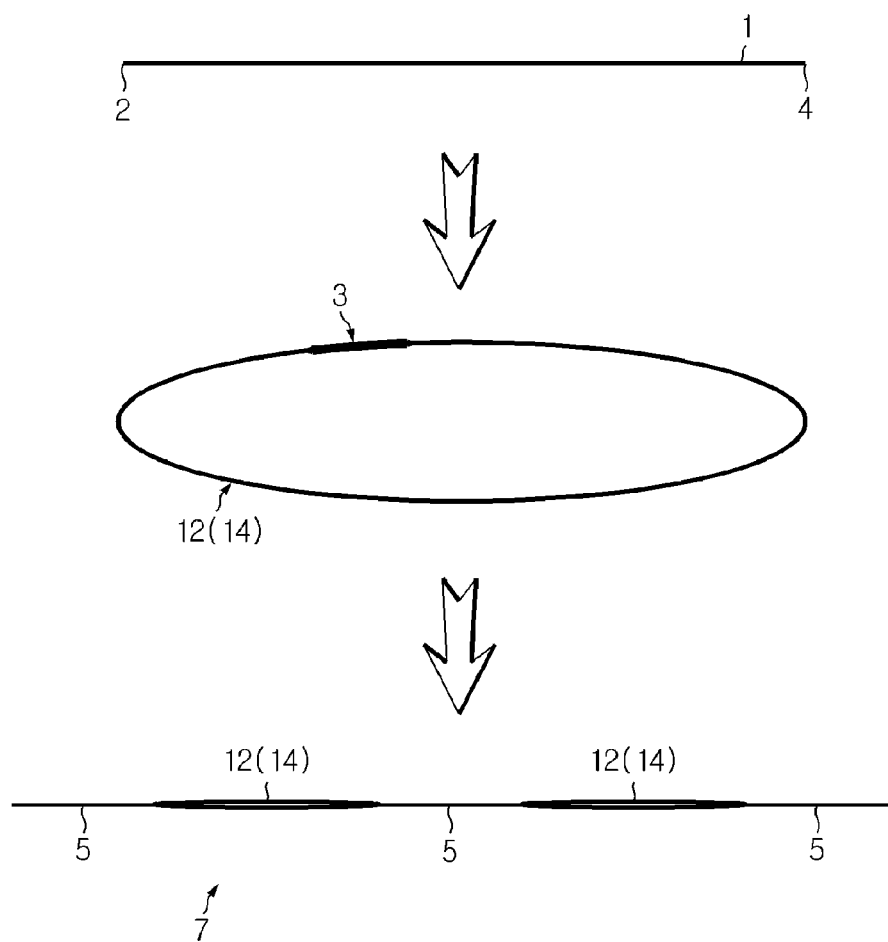
FIG. 5 is a diagram showing an assembly line in which closed-loop wire filaments are formed and connected to guide lines in order to form a stent according to a preferred embodiment of the present invention.
Figure 6:
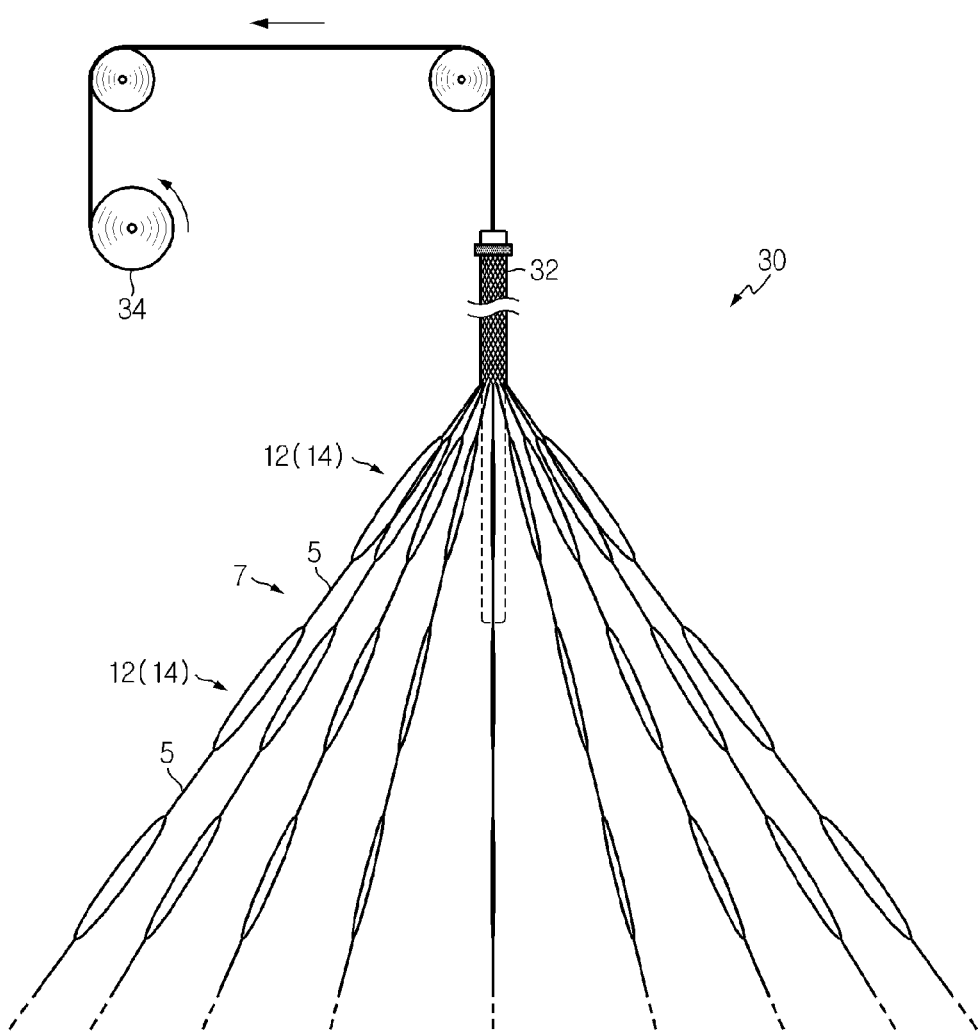
FIG. 6 is a perspective view schematically showing a method for fabricating a stent according to a preferred embodiment of the present invention.

Referring to FIGS. 5 and 6, a fabrication method of the stent according to a preferred embodiment of the present invention will be described.

FIG. 5 shows a method for forming a closed-loop wire filament which may be used in the stent according to the present invention, and a method for forming an assembly line using the same method.

Referring to FIG. 5, the closed-loop wire filaments 12, 14 are formed by welding both ends 2, 4 of a metal wire 1 having a predetermined length. The welding process can be preformed by, for example, a laser bonding process or other generally used bonding processes. Preferably, the ends 2, 4 of the wire 1 are cut obliquely to a longitudinal direction. When the closed-loop wires are formed as described above, contact points 3 are formed on the filaments 12, 14. The contact points 3 are shown in the drawing to be larger than an actual cross-sectional diameter of the wire 1, but the diameter of the contact point 3 is preferably substantially identical to the cross-sectional diameter of the wire 1. A plurality of the closed-loop filaments 12, 14 having a substantially identical length are provided in this manner.

As a conventional medical wire 1 has a very high elasticity, each of the closed-loop filaments 12, 14 is then subject to heat treatment (first heat treatment) to lower the inherent elasticity of the medical wire 1 to the extent that the inherent elasticity is not an obstacle to the braiding process. The heat treatment is preferably performed by the conditions (e.g., temperature or time) known in the art.

With this heat treatment process, the closed-loop filaments 12, 14 may be smoothly braided during a braiding process since the heat treatment prevents them from being entangled or folded due to their elasticity.

As an alternative, both ends of the wire 1 having a constant length may be bended in a round shape, and then the both ends of the wire 1 may be welded. If this method is used, the above-mentioned heat treatment used for fixing a shape of closed-loop filaments may be omitted, and the parallel closed-loop wires may be in close contact with each other.

Next, a plurality of assembly lines 7 are formed, for example, by sequentially connecting guide lines 5 such as threads to both ends of each of the closed-loop filaments 12, 14, wherein the threads includes fiber yarn and cotton yarn which are composed of polyamide, polyester, etc. Here, in the process of connecting the closed-loop filaments 12, 14 to the guide lines 5, a contact point 3 of the closed-loop filaments 12, 14 is preferably positioned as remotely as possible from a point to which the guide line 5 is connected. This is why the connection point 3 is positioned closer to the open ends 16, 18 of the stent 10 as the contact point 3 approaches the guide line 5, and therefore a welding area may be highly damaged by the connection point 3 in use of the stent 10.

FIG. 6 is a diagram schematically showing a braiding apparatus for manufacturing a stent according to a preferred embodiment of the present invention by employing a plurality of assembly lines.

Referring to FIG. 6, the braiding process is performed using a conventional braiding apparatus 30 provided with standard techniques. That is to say, when ends of each of the assembly lines 7 are connected to a circumferential surface of a mandrel 32 having substantially the same diameter as a stent 10 (before expansion) to be manufactured and a predetermined length, the desired stent 10 is braided onto the circumferential surface of the mandrel 32 with the two groups of the assembly lines moving in a zig-zag manner if a braiding bed (not shown), in which a carrier (not shown) that is unwoven by winding of the other end of the assembly line 7 is installed, is transferred into a predetermined shape and also if the mandrel 32 moves through a winding roller 34.

As described above, the diameter of the stent is determined by the diameter of the mandrel 32, and the density of the stent is determined by the number of the assembly lines 7, cycles of a carrier, a take-up speed of a take-up motor, etc. Also, in the braiding process, an angle formed between two groups of the filaments in the stent may be adjusted by controlling the take-up speed which is engaged with the cycles of the carrier. The angle between the filaments in the stent, which is an important factor that determines a bending property of the stent, should be sustained larger than a certain value in order to show good performances in blood vessels.

If the assembly lines 7 are braided in the circumferential surface of the mandrel 32 in this manner, a region of the stent 10 is alternately connected to a region of a braided stent to form a complex braided product, wherein the region of a braided product is formed by entangling the guide lines 5 and the region of the stent 10 is formed by the closed-loop filaments 12, 14. Accordingly, after the braiding process is completed, a stent 10 having a certain shape may be manufactured by separating the complex braided product from the mandrel 32, followed by removing the region of the braided product, composed of the guide lines 5, from the region of the stent 10 using cutting, burning, melting methods, etc.

The stent 10 manufactured by the above-mentioned procedure is subject to heat treatment (second heat treatment) to memorize an inherent stent shape. This heat-treatment step may be performed prior to the step of removing a guide line 5, at the same time as the removal process, or on the finished stent after the process of removing a guide line 5. Also, the heat treatment may be preferably performed under the conditions (e.g., temperature or time) widely known in the art of the stent.

In this embodiment, at least two stents may be continuously fabricated from a plurality of assembly lines having guide line-closed-loop filament-guide line units connected thereto. It is apparent that lengths of the fabricated stents 10 may be different if overlapped lengths of the closed-loop filaments 12, 14 are different from each other in one assembly line 7. It is also possible that only one stent 10 to be braided by connecting one guide line 5 to both ends of one closed-loop filament.

The stents and the methods according to the present invention has the following advantages. First, a welding area can be prevented from being damaged since both open ends of the stent are formed in round regions of the ends of the closed-loop filament. Second, the pre-welding technique enables the stents to be manufactured in a simpler manner compared to the conventional techniques. Third, it is possible to automatize the braiding process and mass-produce the stents with better quality than that of the conventional techniques.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A stent having a hollow tubular structure with open ends which tubular structure is formed by a plurality of filaments woven alternately,
wherein each of the filaments comprises at least one wire, the at least one wire provided in a closed-loop shape, the closed-loop shape having a rounded first end and a rounded second end, the rounded first end and rounded second end connected to each other by a pair of elongate portions extending therebetween, the pair of elongate portions arranged substantially in parallel with each other, the rounded first end and rounded second end being positioned at the open ends of the hollow tubular structure.

2. The stent according to claim 1, wherein the plurality of filaments comprise two groups of pre-formed closed-loop shaped wires which are arranged spirally in a longitudinal direction of the tubular structure and alternate with each other in opposite directions.

3. The stent according to claim 2, wherein each of the two groups of the pre-formed closed loop shaped wires has a pair of parallel wires forming the pair of elongate portions, the pair of parallel wires being substantially in contact with each other.

4. The stent according to claim 2, wherein each of the two groups of the pre-formed closed loop shaped wires has a pair of parallel wires forming the pair of elongate portions, the pair of parallel wires being spaced from each other at predetermined distances.

5. The stent according to claim 2, wherein each of the filaments is made of a biocompatible metal or an alloy thereof.

6. The stent according to claim 2, wherein the tubular structure is formed by braiding and/or winding the filaments.

7. The stent according to claim 1, wherein each of the filaments is made of a biocompatible metal or an alloy thereof.

8. The stent according to claim 1, wherein the tubular structure is formed by braiding and/or winding the filaments.

* * * * *